(12) United States Patent
Karlsson et al.

(10) Patent No.: US 10,022,206 B2
(45) Date of Patent: Jul. 17, 2018

(54) METHOD AND SYSTEM FOR COLORING OR TINTING A PROSTHESIS, AND SUCH A PROSTHESIS

(75) Inventors: Per-Olof Karlsson, Alingsas (SE); Urban Nilsson, Holta (SE)

(73) Assignee: Nobel Biocare Services AG, Kloten (CH)

(*) Notice: Subject to any disclaimer, the term of this patent is extended or adjusted under 35 U.S.C. 154(b) by 592 days.

(21) Appl. No.: 11/576,451

(22) PCT Filed: Sep. 23, 2005

(86) PCT No.: PCT/SE2005/001406
§ 371 (c)(1),
(2), (4) Date: Nov. 5, 2007

(87) PCT Pub. No.: WO2006/036114
PCT Pub. Date: Apr. 6, 2006

(65) Prior Publication Data
US 2008/0193899 A1    Aug. 14, 2008

(30) Foreign Application Priority Data
Sep. 30, 2004  (SE) .................................. 0402360-2

(51) Int. Cl.
*A61C 13/08*  (2006.01)
*A61C 13/00*  (2006.01)

(52) U.S. Cl.
CPC ........ *A61C 13/082* (2013.01); *A61C 13/0003* (2013.01); *A61C 13/0019* (2013.01)

(58) Field of Classification Search
CPC ....... A61C 19/10; A61C 13/082; A61C 13/09; A61C 13/0004; A61C 13/0019; A61C 9/0053; G06F 19/3437
(Continued)

(56) References Cited

U.S. PATENT DOCUMENTS 4,189,325 A   2/1980  Barrett et al.
4,351,853 A   9/1982  Jochum et al.
(Continued)

FOREIGN PATENT DOCUMENTS

EP  0 311 214   4/1989
EP  0 774 933   12/2000
(Continued)

OTHER PUBLICATIONS

International Search Report for Application No. PCT/SE 2005/001406 (the PCT counterpart of the parent application).

*Primary Examiner* — Matthew Nelson
(74) *Attorney, Agent, or Firm* — Knobbe Martens Olson & Bear LLP

(57) ABSTRACT

A method, system, and dental prosthesis are provided to facilitate simulation of the natural appearance of teeth. The prosthesis can be formed to include a component to which an aesthetic coating, such as a coloring or tint, can be applied. Further, the prosthesis can include a porcelain coating disposed on the outer surface thereof, and on top of the aesthetic coating, such that the aesthetic coating can be visible through the porcelain coating of the prosthesis. During production, the crown can be coated with a metal and/or ceramic powder by means of a powder printer that can be controlled by computer equipment. A practical and rapid application function can be obtained to produce an extremely natural-looking result.

14 Claims, 4 Drawing Sheets

(58) Field of Classification Search
USPC .................................... 433/202.1, 203.1, 26
See application file for complete search history.

(56) References Cited

U.S. PATENT DOCUMENTS

| | | | |
|---|---|---|---|
| 4,626,514 A | | 12/1986 | Watanabe et al. |
| 4,654,007 A | | 3/1987 | Sigler et al. |
| 4,799,887 A | | 1/1989 | Hakamatsuka et al. |
| 5,104,319 A | | 4/1992 | Evans et al. |
| 5,171,147 A | | 12/1992 | Burgess |
| 5,240,414 A | | 8/1993 | Thompson |
| 5,248,258 A | | 9/1993 | Feldman |
| 5,263,858 A | | 11/1993 | Yoshida et al. |
| 5,308,243 A | * | 5/1994 | Emmons ............... A61C 13/09 433/203.1 |
| 5,382,164 A | | 1/1995 | Stern |
| 5,501,600 A | | 3/1996 | Johnson |
| 5,549,476 A | | 8/1996 | Stern |
| 5,565,152 A | | 10/1996 | Od En et al. |
| 5,993,214 A | | 11/1999 | Persson |
| 6,033,222 A | | 3/2000 | Schneider et al. |
| 6,133,174 A | * | 10/2000 | Brodkin ............... C03C 4/0021 106/35 |
| 6,322,728 B1 | | 11/2001 | Brodkin et al. |
| 6,328,567 B1 | | 12/2001 | Morris et al. |
| 6,334,775 B2 | | 1/2002 | Xu et al. |
| 6,354,836 B1 | | 3/2002 | Panzera et al. |
| 6,358,047 B2 | * | 3/2002 | Lehmann ............... A61C 19/10 356/408 |
| 6,375,729 B1 | | 4/2002 | Brodkin et al. |
| 6,379,593 B1 | * | 4/2002 | Datzmann ............ A61C 13/0022 264/16 |
| 6,428,614 B1 | | 8/2002 | Brodkin et al. |
| 6,455,451 B1 | | 9/2002 | Brodkin et al. |
| 6,465,106 B1 | | 10/2002 | Petticrew |
| 6,485,849 B2 | | 11/2002 | Petticrew |
| 6,488,503 B1 | * | 12/2002 | Lichkus ............... A61C 13/087 264/19 |
| 6,575,751 B1 | | 6/2003 | Lehmann et al. |
| 6,599,125 B1 | | 7/2003 | Freilich et al. |
| 6,645,285 B2 | | 11/2003 | Brodkin et al. |
| 6,666,684 B1 | | 12/2003 | Names |
| 6,755,646 B2 | | 6/2004 | Zun |
| 6,761,760 B2 | | 7/2004 | Brodkin et al. |
| 6,786,726 B2 | | 9/2004 | Lehmann et al. |
| 6,808,659 B2 | | 10/2004 | Schulman |
| 6,818,573 B2 | | 11/2004 | Petticrew |
| 6,821,462 B2 | | 11/2004 | Schulman et al. |
| 6,878,456 B2 | | 4/2005 | Castro et al. |
| 6,979,496 B2 | | 12/2005 | Haymann et al. |
| 6,984,261 B2 | | 1/2006 | Cummings et al. |
| 6,994,545 B2 | | 2/2006 | Mrotzek et al. |
| 7,011,522 B2 | | 3/2006 | Panzera et al. |
| 7,029,279 B2 | * | 4/2006 | Schomann ............ A61C 13/0004 433/203.1 |
| 7,064,830 B2 | * | 6/2006 | Giorgianni ............... G01J 3/508 356/402 |
| 7,153,135 B1 | * | 12/2006 | Thomas ............... A61B 5/1077 433/213 |
| 7,166,256 B2 | | 1/2007 | Lindigkeit |
| 7,179,265 B2 | | 2/2007 | Sims et al. |
| 7,279,238 B2 | | 10/2007 | Brodkin |
| 7,351,281 B2 | | 4/2008 | Hermansson et al. |
| 7,463,757 B2 | * | 12/2008 | Luo ........................... G01J 3/50 382/128 |
| 7,494,539 B2 | | 2/2009 | Ikushima et al. |
| 7,497,983 B2 | | 3/2009 | Khan et al. |
| 7,581,953 B2 | | 9/2009 | Lehmann et al. |
| 7,790,073 B2 | | 9/2010 | Culp |
| 7,955,159 B2 | | 6/2011 | Heinz et al. |
| 8,052,424 B2 | | 11/2011 | Cameron et al. |
| 8,105,084 B2 | | 1/2012 | Lehmann et al. |
| 8,110,035 B2 | | 2/2012 | Chu et al. |
| 2001/0049083 A1 | * | 12/2001 | Jung ..................... A61B 5/4547 433/29 |
| 2002/0064745 A1 | * | 5/2002 | Schulman .......... A61C 13/0003 433/2 |
| 2003/0031984 A1 | | 2/2003 | Rusin et al. |
| 2004/0067465 A1 | * | 4/2004 | Schomann ......... A61C 13/0004 433/26 |
| 2004/0214141 A1 | | 10/2004 | Neuber |
| 2004/0224278 A1 | * | 11/2004 | Zun ........................ A61C 19/10 433/26 |
| 2004/0232576 A1 | * | 11/2004 | Brodkin ................. C03C 3/091 264/16 |
| 2004/0243481 A1 | * | 12/2004 | Bradbury ............... G06Q 50/22 705/26.1 |
| 2005/0064369 A1 | | 3/2005 | Zel et al. |
| 2005/0112522 A1 | * | 5/2005 | Riley ..................... A61C 19/10 433/26 |
| 2005/0115460 A1 | | 6/2005 | Petticrew |
| 2005/0123880 A1 | | 6/2005 | Grundler et al. |
| 2005/0181330 A1 | | 8/2005 | Kim et al. |
| 2005/0202368 A1 | | 9/2005 | Ganley |
| 2005/0261795 A1 | | 11/2005 | Ghosh et al. |
| 2006/0099552 A1 | | 5/2006 | Van Der et al. |
| 2006/0172263 A1 | | 8/2006 | Quadling et al. |
| 2006/0204932 A1 | * | 9/2006 | Haymann .......... A61C 13/0022 433/201.1 |
| 2006/0290019 A1 | | 12/2006 | Neuber |
| 2007/0003908 A1 | | 1/2007 | Porter |
| 2007/0062410 A1 | | 3/2007 | Thiel et al. |
| 2008/0050699 A1 | | 2/2008 | Zhang et al. |
| 2008/0164254 A1 | | 7/2008 | Hegenbarth |
| 2008/0199826 A1 | | 8/2008 | Jia et al. |
| 2008/0254412 A1 | | 10/2008 | Korrodi et al. |
| 2008/0318189 A1 | | 12/2008 | Brodkin et al. |
| 2009/0004630 A1 | | 1/2009 | Van Der et al. |
| 2009/0023112 A1 | | 1/2009 | Ganley et al. |
| 2009/0087815 A1 | | 4/2009 | Oyama et al. |
| 2009/0130634 A1 | | 5/2009 | Ganley et al. |
| 2009/0168063 A1 | | 7/2009 | Kobayashi |
| 2009/0227438 A1 | | 9/2009 | Fukatani et al. |
| 2009/0274994 A1 | | 11/2009 | Jung et al. |
| 2009/0275000 A1 | | 11/2009 | Jung et al. |
| 2009/0298017 A1 | | 12/2009 | Boerjes et al. |
| 2010/0015574 A1 | | 1/2010 | Van der Zel et al. |
| 2010/0173257 A1 | | 7/2010 | Yamamoto et al. |
| 2010/0221682 A1 | | 9/2010 | Burger et al. |
| 2010/0221683 A1 | | 9/2010 | Franke et al. |
| 2010/0233658 A1 | | 9/2010 | Ganley et al. |
| 2010/0297586 A1 | | 11/2010 | Culp |
| 2011/0104642 A1 | | 5/2011 | Luksch et al. |
| 2011/0104643 A1 | | 5/2011 | Giordano |
| 2011/0171604 A1 | | 7/2011 | Durbin et al. |
| 2011/0183297 A1 | | 7/2011 | Thiel et al. |
| 2011/0200966 A1 | | 8/2011 | Heinz et al. |
| 2011/0244429 A1 | | 10/2011 | Waizenegger et al. |
| 2011/0256507 A1 | | 10/2011 | Chiu et al. |
| 2011/0306017 A1 | | 12/2011 | Tanaka |
| 2012/0015328 A1 | | 1/2012 | Giasson et al. |

FOREIGN PATENT DOCUMENTS

| | | |
|---|---|---|
| EP | 1 252 867 | 10/2002 |
| EP | 1396237 A1 | 3/2004 |
| EP | 1 927 325 | 6/2008 |
| EP | 1 972 298 | 9/2008 |
| EP | 2361601 A1 | 8/2011 |
| JP | 2003/340813 | 12/2003 |
| SE | 501333 C2 | 1/1995 |
| WO | WO 2002/085241 | 10/2002 |
| WO | WO 2003/061513 | 7/2003 |
| WO | WO 2007/053084 | 5/2007 |
| WO | WO 2009/111041 | 9/2009 |

* cited by examiner

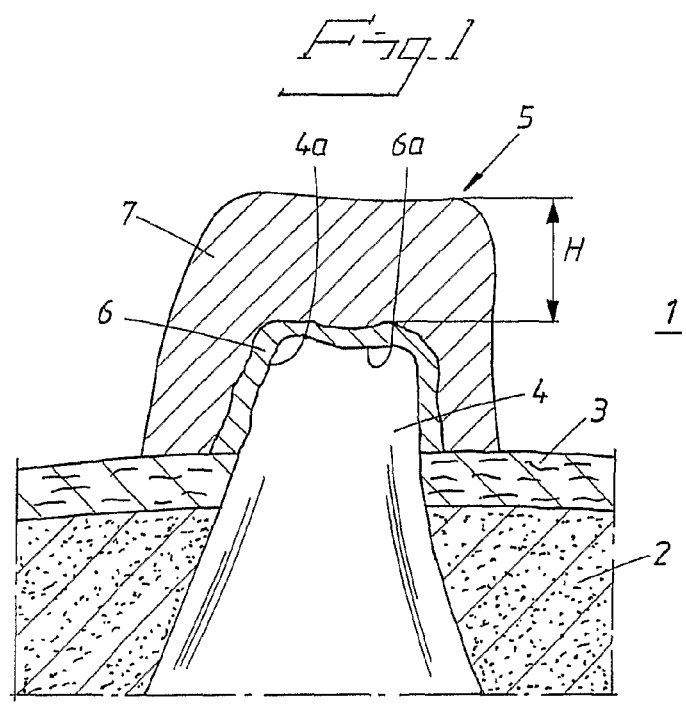
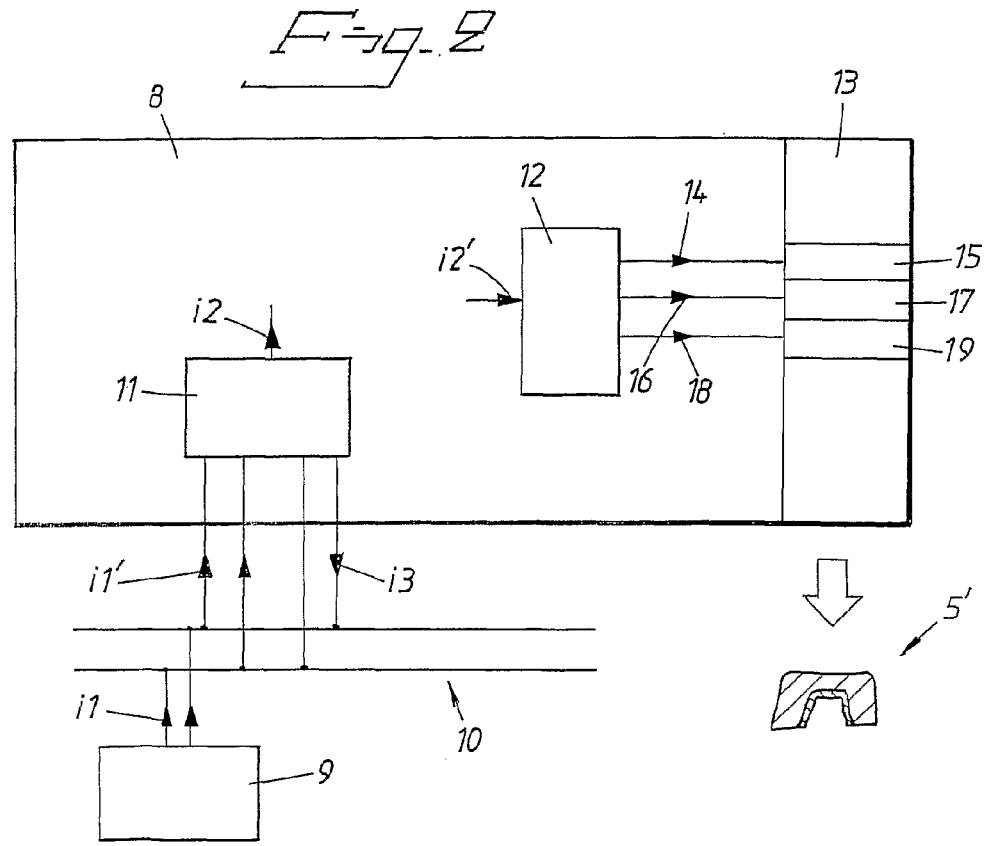

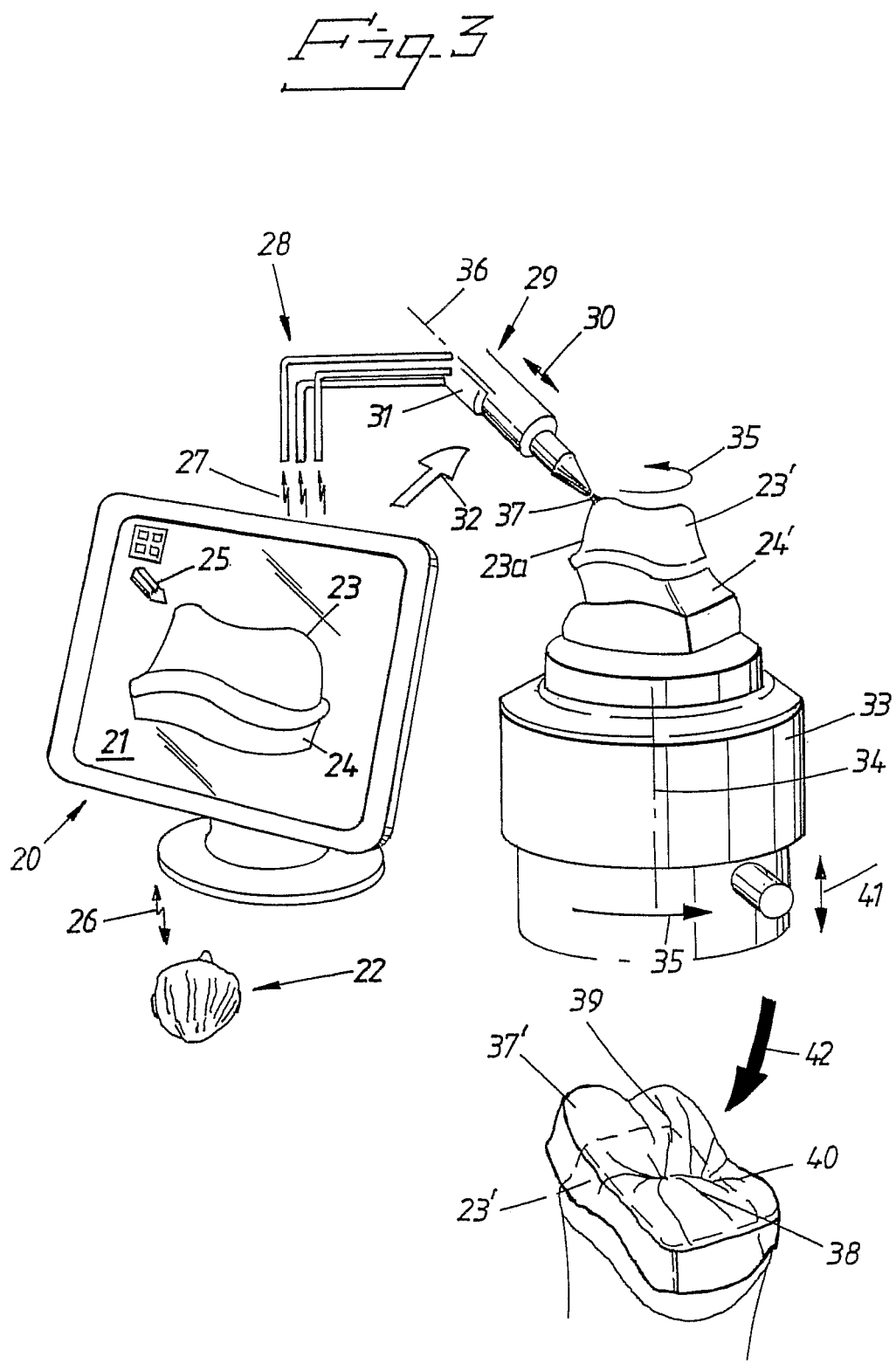

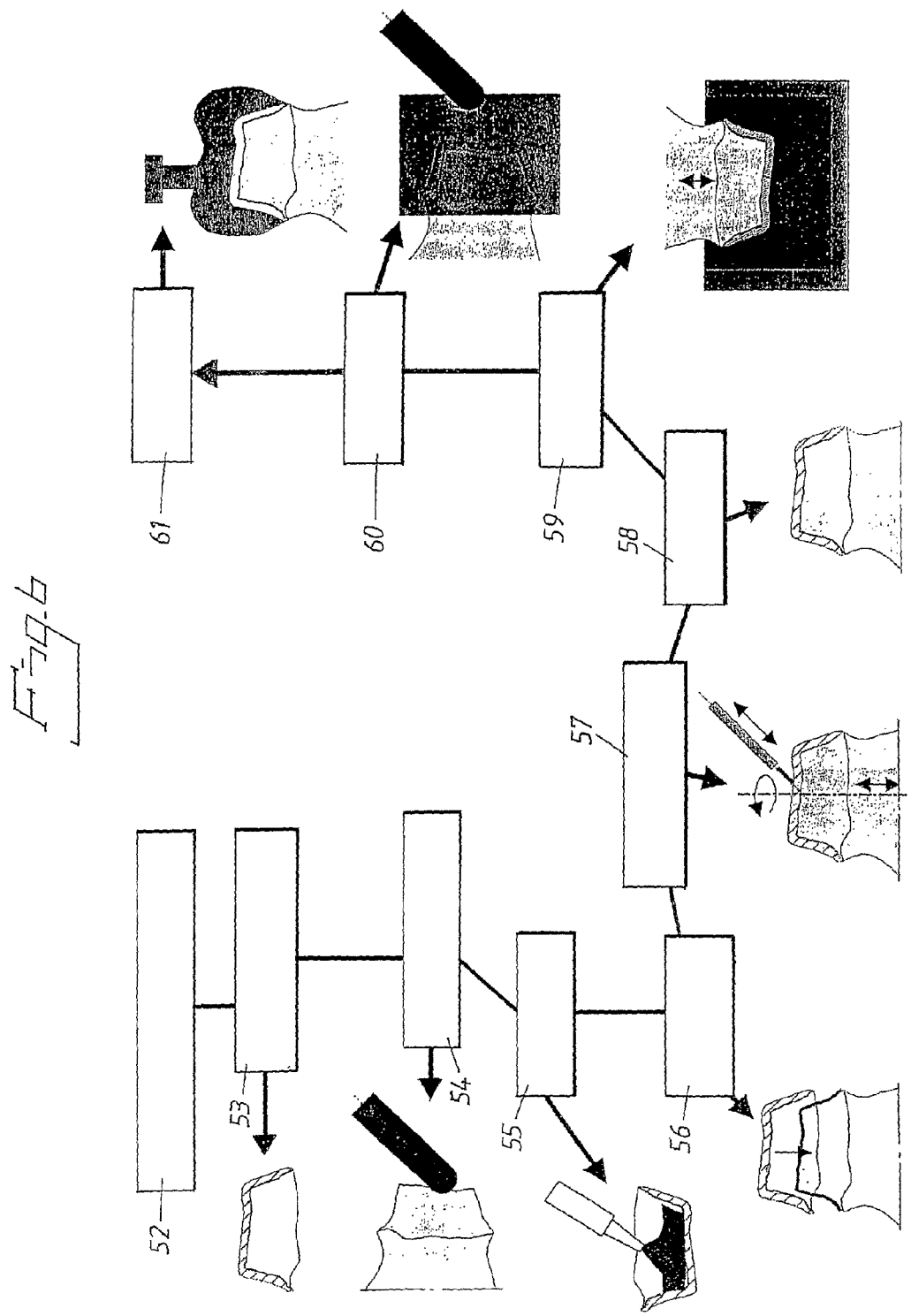

METHOD AND SYSTEM FOR COLORING OR TINTING A PROSTHESIS, AND SUCH A PROSTHESIS

CROSS-REFERENCE TO RELATED APPLICATIONS

This application is a U.S. National Phase of International Application No. PCT/SE2005/001406, filed Sep. 23, 2005, which claims priority to Swedish Patent Application No. 0402360-2, filed Sep. 30, 2004, each of which is hereby incorporated by reference in its entirety.

BACKGROUND

Field of the Inventions

The present inventions relate to a method, apparatus, and system for obtaining on a dental prosthesis, and more specifically, a dental prosthesis that has, for example, a porcelain-coated crown with a coloring or tint that is visible from the outside of the prosthesis.

Description of the Related Art

It is known in the art that dental products such as porcelain-coated crowns can be manually colored or painted. It is also known, from other fields outside dentistry, that some components can be spray-coated with metal powder, such as in the Arcam® system, for example. Further, fully automated manufacturing systems for dental components have also been developed. For example, the Applicant of the present application uses the PROCERA® system. Other such systems and components are disclosed in Swedish patent application 0302971-1.

European Patent Application Publication EP1396237A1, entitled Strengthened Ceramic Restoration, also discloses a system for producing fully ceramic tooth restorations where coloring can be achieved by immersing the tooth restoration in a suitable color.

SUMMARY

An aspect of at least one of the embodiments disclosed herein is the realization that in the coloring and tinting dental products or parts thereof, there is a marked need to improve the techniques used and to speed up the manufacturing procedure. It is also preferable to allow the continued use of the techniques and equipment that are presently employed in the dental field without making too many modifications. In addition, there is a need in the art to substantially reduce production time associated with such manufacturing procedures. Thus, an aspect of at least one of the embodiments disclosed herein is the realization that in order to reduce the production time, time-consuming painting and immersing operations should be avoided. One of the objects of the present inventions is to remedy this problem, among others.

In coloring and tinting, it is important to be able to optimize the coloring and tinting of a dental prosthesis to the environment within the oral cavity in which the prosthesis is to be used. The teeth of each patient have tints which are dependent both on the individual and on age, and there are considerable variations. It may be expedient to use general knowledge and experience to obtain a correct and natural-looking color. It is important in particular to accurately simulate and maintain the region of the front teeth. This region in particular requires the creation, for example, of a fully colored tooth which will merge with the other teeth in a natural-looking and optimal manner. Unfortunately, earlier work involving application by painting must be transferable to computer equipment environment which is used for natural-looking coloring, decoration, etc. The object of the invention is to remedy this problem too.

In accordance with an embodiment of the present inventions, it is contemplated that during production, the crown can be coated with metal and/or ceramic powder by means of a powder printer (such as a pistol, nozzle, etc.) that can be controlled by computer equipment.

In one aspect of a method of producing the crown can begin with an inner shape of the crown being milled out. The crown can then be applied on a die. On its top face, the crown can be coated with said metal and/or powder. The coating is dried thereafter, and molten wax is applied and profiled. The profiled wax is placed, together with the crown, in a cuvette and the wax is removed with heat. A space is thus created in the powder-coated surface, to which space the porcelain material is introduced and allowed to set.

In an alternative embodiment, the porcelain-coated crown is built up with a number of layers applied on one another by means of spraying of metal(s) and/or ceramic(s) in powder form of each layer. Between or at the spraying operations, a function is initiated or included for coloring or tinting. The overall coloring or tinting can be effected by combination of coloring or tinting constellations applied on top of one another or after one another.

In yet another embodiment, a dental prosthesis is provided, preferably in the form of a porcelain-coated crown. The prosthesis can comprise an inner coloring or tinting consisting of applied and dried metal and/or ceramic powder. In a preferred embodiment, the inner coloring or tinting can consist of layers of powder placed on top of one another. The coloring or tint can be chosen as a function of the coloring adjoining the prosthesis and/or teeth or can be chosen for decorative purposes.

According to another embodiment, a system is provided in which a color printer (such as a pistol, nozzle, etc.) can be configured, as a function of activation, to emit powder jets directed toward the prosthesis or prosthesis part in question. The activations can be controlled or initiated by means of information from computer equipment which interacts with a user and, by actuations of the computer equipment, controls the coloring or tinting.

In other embodiments of the system, information from the computer equipment can be transmitted to a production unit which can consist of an essentially fully automated manufacturing system, for example, in the form of Procera®, where the coloring or tinting functions can be input as a module unit in the other processing functions of the manufacturing system. An example of such a manufacturing system is described in abovementioned Swedish Patent Application 0302971-7. The color printer or the like can work essentially at approximately a 45 degree angle with respect to the actual surface to be coated in or on the dental prosthesis or the prosthesis part.

By means of what has been proposed above, it is possible to obtain much more rapid and, generally speaking, more generalized coloring and tinting. The colors or tints can be built up from the inside, and the porcelain is transparent and, as a function of its configuration, can, together with the configuration of the crown, produce different refractions and appearances which in an excellent way simulate the natural appearance. The new advantages are especially marked in the region of the front teeth.

The time factor is less critical, when using the invention, compared to previously used painting operations. Charts and library information can be organized based on the experience which is gradually gained in the field, and the fully automated manufacturing systems can be provided with CAD modules which can be adapted to already existing modules. The colors can be sprayed on and dried before, for example, pressing of the porcelain. The coloring can be diffuse and natural-looking and can be produced inside the prosthesis. The result can also be advantageous from the point of view of strength, and reflections in the porcelain part can be used and accentuated as a function of its thickness and its actual extent and the extent in relation to the crown. In the computer equipment, the coloring can be simulated with different color constellations placed on top of one another.

BRIEF DESCRIPTION OF THE DRAWINGS

The abovementioned and other features of the inventions disclosed herein are described below with reference to the drawings of the preferred embodiments. The illustrated embodiments are intended to illustrate, but not to limit the inventions. The drawings contain the following figures:

FIG. 1 shows a side cross-sectional view of parts of a jaw bone, gum, a ground tooth remnant, and, arranged on the remnant, a dental prosthesis in the form of a porcelain-coated crown, according to an embodiment of the present invention.

FIG. 2 is a block diagram illustrating the connection of novel equipment to an existing and essentially fully automated manufacturing system of the PROCERA® type, according to another embodiment.

FIG. 3 is an oblique top perspective view of a system for application of powder to a crown by means of a computer-controlled coloring device, and where upper parts of the crown are additionally shown enlarged, according to yet another embodiment.

FIG. 6 is a flow chart of a manufacturing method for production of a porcelain-coated crown, according to yet another embodiment.

DETAILED DESCRIPTION OF THE PREFERRED EMBODIMENTS

Figure 4:
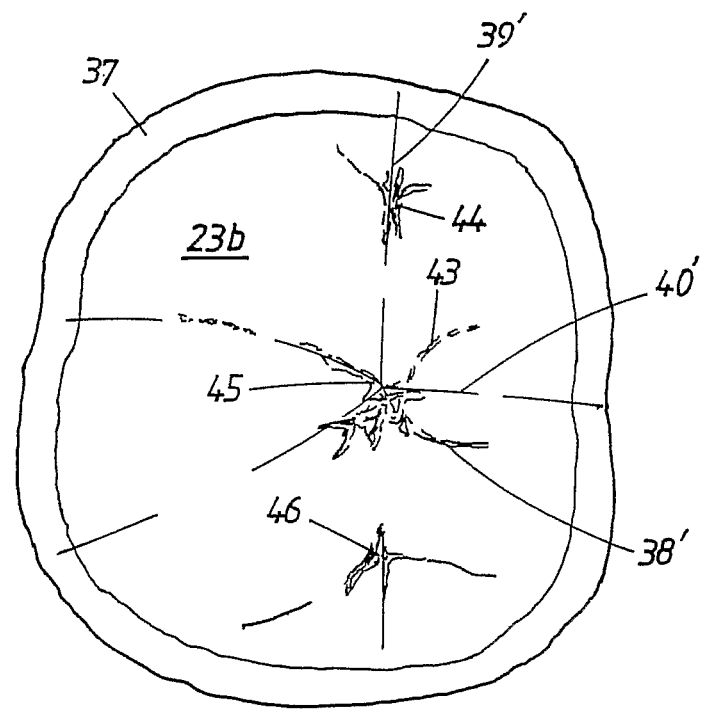
FIG. 4 is a top view of powder applied to a top face of the crown by the color printer according to FIG. 3.

With reference to FIG. 1, there is illustrated a human oral cavity 1 and a jaw bone 2. The jaw bone 2 includes a gum 3. A ground-down tooth or tooth remnant 4 and an embodiment of a dental prosthesis 5 are also shown. In the embodiment shown, the prosthesis 5 has the form of a crown 6 and a porcelain part or porcelain lining 7 on its outside. The inner surface 6a of the crown 6 can adjoin the outer surface 4a of the tooth 4 with great precision.

The porcelain-coated crown 4 can be manufactured in an essentially fully automated manufacturing system 8, according to the embodiment illustrated in FIG. 2. In accordance with an embodiment, information concerning the crown 6 and the porcelain part 7, as shown in FIG. 1, is simulated, initiated, and/or transmitted to the system 8 with equipment 9, which can be customer-based equipment. For example, the transmission can be via a public telephone network 10 and/or computer network (Internet).

As shown in FIG. 2, the initiation and the transmission of information are symbolized by i1. The information can be received in the system 8 with information signals i1' which can be input to receiving equipment 11. The receiving equipment 11 can convey the information onward to a unit 12 via transmission signals i2.

According to another embodiment, the system 8 can confirm receipt with the customer location 9 and can be configured to transmit further information in this regard. Signals i3 can therefore be transmitted from the system 8 to the customer 9 from the unit 11.

The system 8 is provided with a module unit 13 which is controlled by the control unit 12. The control unit 12 can include a color selection 14 which can be passed to a unit 15 in the module unit 13. The module unit 13 can also receive information regarding the crown 6 and the porcelain part 7, such as the number of layers and the layer thicknesses, as has been symbolized by arrow 16 and part unit 17. In some embodiments, parameters such as drying times, etc., can be affected by means of control information 18 and part unit 19, etc.

The final production in the system 8 can result in the prosthesis or prosthesis part 5' which is returned to the customer location 9 in a known manner, such as by mail or recorded delivery, courier, etc. The customer location 9 can be included in the information provided to the computer equipment in a known manner.

FIG. 3 is an oblique top perspective view of a system for application of powder to a crown by means of a computer-controlled coloring device, according to yet another embodiment. As shown in FIG. 3, the system can include computer equipment 20, including a computer screen 21, which can be used by a user (dental technician) 22 to initiate, simulate, and/or illustrate a crown 23 which is applied on a die 24. The coloring device can be shown on the screen 21, for example, by element number 25.

The computer equipment 20 can be interactive to allow the user 22 to prepare the crown 23. The interaction between the computer equipment 20 and the user 22 can be wireless, for example by voice, as has been indicated by 26. Alternatively, the interactive use can be via a keyboard (not shown) in a known manner. The information from the computer equipment 20 concerning the coloring can be sent digitally, as has been symbolized by 27. The system can utilize operate with a number of base colors, and connection lines for these are shown by 28. In this regard, the coloring device can be a color printer 29, and can have directions of movement as illustrated by the arrows 30. The color printer 29 can comprise a mixing unit 31 for mixing the colors to obtain the desired colouring or tint defined by the computer and has been illustrated by an arrow 32.

As shown in FIG. 3, a real die 24' can be provided which corresponds to the die 24 illustrated on the screen 21. In a corresponding manner, the crown 23 on the screen 21 is also shown as a real crown 23'. The die 24' can be mounted on a tool 33 which can be rotatable about its longitudinal axis 34, for example, in a counterclockwise direction 35. The tool 33 and the color printer 29 can be moved relative to one another in the vertical direction, and the longitudinal axis 36 of the color printer 29 can adopt an inclination which is essentially approximately 45 degrees with respect to an outer surface 23a of the real crown 23' during application of powder 37' with the colors, optionally in (glycerol-based) liquid form.

In one, the real crown 23' can be produced as described below. The crown 23' located inside the porcelain part 37 can be coated, in accordance with the lower part of FIG. 3, with color powder in different strips 38, 39 and quantities such that a natural-looking reproduction is obtained for the porcelain-coated crown when it is placed in the patient's mouth. Potential upward and downward movements of the tool 33 are indicated by the arrows 41, and transfer of the position of the crown 23' in cooperation with the color printer 29 to the position inside the porcelain part has been shown by the arrow 42.

With reference now to the embodiment shown in FIG. 4, a top surface 23b of a porcelain coated part 37 can be coated with different strips 38', 39' and 40' of coloring. Likewise, different accumulations of colors 43, 44, 45 and 46 can be applied. The patterns can reproduce, together with the colors and the position of the strips, the overall coloring or tinting which is desired. The overall coloring can be based on tests and on experience which can be set out in charts or tables to be used in the different circumstances that arise. The extent of the top surface 23b which corresponds to the extent of the porcelain part 37 can be included in the coloring pattern. A further parameter is the height H which is shown in FIG. 1 between the tops of the crown 23' and of the porcelain part 37, and is an important consideration for the final result.

Figure 5:
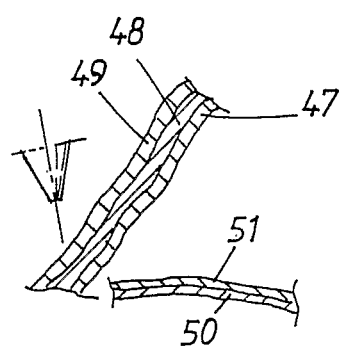
FIG. 5 is a side cross-sectional view illustrating build-up of layers on the crown and layered application of powder/color thereto, according to yet another embodiment.

FIG. 5 is intended to show an embodiment wherein the crown 23' has been built up with different layers 47, 48 and 49 with the aid of a color printer 29 (see FIG. 3) or corresponding equipment. The color powder illustrated in FIG. 4 can also be applied in different layers, of which two have been shown by 50 and 51 in FIG. 5. These layers 50, 51 can be applied through use of a so-called internal stain modifier. By combining the layers 50, 51 and placing these on top of one another, the result of the final coloring or tinting can be influenced.

In an embodiment, the color printer 29 shown in FIG. 3 can thus be used, on the one hand, for building up the crown 23' and, on the other hand, for coloring the crown 23'. Alternatively, two different appliances can be used. The same technique can be used in the production or simulation of the crown 23' on the computer screen 21, and the simulation function can be program-controlled.

With reference now to FIG. 6, there is illustrated a flow chart of a manufacturing method for production of a porcelain-coated crown, according to yet another embodiment In one embodiment of the method, in a first step 52 of the method, an order is placed at the production unit 8 (shown in FIG. 2). The production unit 8 runs data which is forwarded to a production system. In a manufacturing step 53, a crown is produced according to a previously known method, for example made of aluminium oxide or zirconium oxide. In a subsequent step 54, an inner shape of the crown is milled out. Impression compound can then be introduced into the crown in a step 55, and the impression is used to secure the crown on the die.

In addition, as represented by step 56, the crown can be mounted on the die. Thereafter, painting can be carried out in accordance with the above in a step 57, and drying and/or hardening of the particular color in a step 58. As in the previously known production procedure, this is followed by application of molten wax, milling of the outer shape in the hardened wax, and application of casting channels in the wax according to steps 59, 60 and 61. In accordance with the above, the dental technician/person placing the order paints or colors the crown in a CAD environment. Color data can thereafter be coupled to the crown, and the information on this is transmitted digitally to the production unit 8 via the order in a manner known per se. The color printer at the production unit can apply the colors to the crown according to a pattern, as has been specified by the dental technician. The color printer is thus located at the production unit 8.

In accordance with the invention, a number of basic colors are used, for example five to fifteen, preferably nine or ten, and these can be dental base colors known to the dental technician, such as dark, brown, peach, caramel, white, violet, stain orange, etc.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

The invention claimed is:

1. A method for producing a porcelain coated dental prosthesis, the method comprising:
   displaying an initial display of a CAD model of the dental prosthesis on a computer screen of a computer in a CAD environment;
   via an interactive use between the user and the computer, coloring the initial display of the CAD model in the CAD environment according to a pattern specified by the user, wherein the pattern comprises a first color constellation placed on top of a second color constellation, the second color constellation being different from the first color constellation;
   simulating, in the CAD environment, to generate a simulated display, the first color constellation placed on top of the second color constellation;
   based on at least the simulated display, selecting and specifying at least one of a coloring and a tint in the CAD environment to determine at least one selected coloring and tint for application to the prosthesis; and
   providing data to a production unit, the data being representative of at least one selected coloring and tint,
   wherein said production unit comprises a printer including a jet sized and configured to selectively emit a powder directed toward a component of the dental prosthesis, and wherein said production unit further comprises a computer unit including a process for controlling the jet using said provided data,
   wherein said method further comprises rotating said jet and said component of the prosthesis relative to one another about a longitudinal axis of said component of the prosthesis and emitting from said jet a powder to said component of the prosthesis using the data provided to the printer for controlling said jet to provide an aesthetic coating comprising at least one of a coloring and a tint that is visible from outside the dental prosthesis.

2. The method of claim 1, further comprising simulating production of the dental prosthesis in a CAD environment on a computer.

3. The method of claim 2, wherein the coloring step comprises simulating coloring with different color constellations placed on top of one another.

4. The method of claim 1, wherein the production unit comprises an automated manufacturing system, and the step of providing data comprises providing data to the automated manufacturing system.

5. The method of claim 1, wherein at least one of the coloring and the tint is determined utilizing a plurality of base colors.

6. The method of claim 1, wherein the step of selecting and specifying at least one of a coloring and a tint in the CAD environment is performed by a technician.

7. The method of claim 1, further comprising displaying on the computer screen the CAD model of the dental prosthesis with the selected and specified coloring or tint.

8. The method of claim 1, further comprising receiving control information at a control unit, the control information comprising at least one of a number of layers and a layer thickness of the dental prosthesis.

9. The method of claim 8, wherein displaying a CAD model of the dental prosthesis on a computer screen in a CAD environment uses at least the control information.

10. The method of claim 1, wherein the data instructs the production unit to place a first color constellation on top of a second color constellation.

11. The method of claim 1, wherein at least one or both of the first and second color constellations simulate an inner coloring or tinting of the prosthesis.

12. The method of claim 1, wherein the powder is in dry form.

13. The method of claim 1, wherein the powder is suspended in a liquid.

14. The method of claim 1, wherein the component is a surface of the dental prosthesis.

* * * * *